US010221987B2

(12) United States Patent
Vallapuzha et al.

(10) Patent No.: US 10,221,987 B2
(45) Date of Patent: Mar. 5, 2019

(54) MANAGING INFRASTRUCTURE DATA

(71) Applicant: RedZone Robotics, Inc., Pittsburgh, PA (US)

(72) Inventors: Subramanian Vallapuzha, Pittsburgh, PA (US); Eric C. Close, Sewickley, PA (US)

(73) Assignee: RedZone Robotics, Inc., Pittsburgh, PA (US)

( * ) Notice: Subject to any disclaimer, the term of this patent is extended or adjusted under 35 U.S.C. 154(b) by 0 days.

(21) Appl. No.: 14/881,084

(22) Filed: Oct. 12, 2015

(65) Prior Publication Data

US 2016/0171442 A1 Jun. 16, 2016

Related U.S. Application Data

(62) Division of application No. 13/654,388, filed on Oct. 17, 2012, now Pat. No. 9,156,105.

(60) Provisional application No. 61/547,908, filed on Oct. 17, 2011.

(51) Int. Cl.
| | | |
|---|---|---|
| *F16L 55/00* | (2006.01) | |
| *F16L 55/32* | (2006.01) | |
| *B23K 9/127* | (2006.01) | |
| *G01B 11/24* | (2006.01) | |
| *G01N 21/954* | (2006.01) | |
| *G06Q 10/06* | (2012.01) | |
| *G06Q 10/10* | (2012.01) | |
| *B23K 9/095* | (2006.01) | |

(52) U.S. Cl.
CPC .......... *F16L 55/32* (2013.01); *B23K 9/1274* (2013.01); *G01B 11/24* (2013.01); *G01N 21/954* (2013.01); *G06Q 10/06* (2013.01); *G06Q 10/10* (2013.01); *B23K 9/0956* (2013.01); *G01N 2021/9544* (2013.01); *G01N 2021/9548* (2013.01)

(58) Field of Classification Search
None
See application file for complete search history.

(56) References Cited

U.S. PATENT DOCUMENTS

| | | | | |
|---|---|---|---|---|
| 7,869,944 B2* | 1/2011 | Deaton | ................... | G01C 15/00 |
| | | | | 701/491 |
| 8,595,051 B2* | 11/2013 | Below | ................... | G06Q 10/06 |
| | | | | 705/7.38 |
| 2002/0091991 A1* | 7/2002 | Castro | ....................... | G06F 9/06 |
| | | | | 717/106 |

(Continued)

OTHER PUBLICATIONS

Beason, M., Solo Robot and ICOM3 Software Pilot for: Dallas Water Utilities City of Dallas, presentation, 2010, 21 pages.

*Primary Examiner* — Gurkanwaljit Singh
(74) *Attorney, Agent, or Firm* — Cafardi, Ferguson, Wyrick, Weis and Stotler LLC; Andrew M. Gabriel

(57) ABSTRACT

One aspect provides a method, including: storing an infrastructure project summary report with one or more other infrastructure project reports pooled in a database of project summary reports; the infrastructure project report being prepared via accessing fluid conveyance infrastructure summary data describing a condition of a fluid conveyance infrastructure segment; and using a processor of an electronic device to match the infrastructure project summary report with one or more other infrastructure project reports pooled in the database of project summary reports. Other aspects are described and claimed.

15 Claims, 8 Drawing Sheets

(56) References Cited

U.S. PATENT DOCUMENTS

| | | | | |
|---|---|---|---|---|
| 2003/0023404 | A1* | 1/2003 | Moselhi | G01N 21/954 702/181 |
| 2005/0127285 | A1* | 6/2005 | Kampf | G01N 33/442 250/281 |
| 2005/0144592 | A1* | 6/2005 | Below | G06Q 10/06 717/124 |
| 2006/0178917 | A1* | 8/2006 | Merriam | G06Q 10/06312 705/7.22 |
| 2006/0201546 | A1* | 9/2006 | Yokoyama | H01L 27/14621 136/263 |
| 2006/0235611 | A1* | 10/2006 | Deaton | G01C 15/00 701/491 |
| 2006/0290779 | A1* | 12/2006 | Reverte | E03F 7/10 348/84 |
| 2007/0278196 | A1* | 12/2007 | James | B23K 31/12 219/130.01 |
| 2009/0193899 | A1* | 8/2009 | Panetta | G01N 29/07 73/622 |
| 2010/0094606 | A1* | 4/2010 | Richard | G01B 17/06 703/2 |
| 2010/0145143 | A1* | 6/2010 | Salomon | B08B 9/049 600/104 |
| 2011/0036560 | A1* | 2/2011 | Vail, III | E21B 28/00 166/87.1 |
| 2011/0119193 | A1* | 5/2011 | McLees | G06Q 10/00 705/301 |
| 2011/0244125 | A1* | 10/2011 | Weisenberg | B05D 7/22 427/236 |
| 2012/0212326 | A1* | 8/2012 | Christiansen | H04Q 9/00 340/10.1 |

* cited by examiner

MANAGING INFRASTRUCTURE DATA

CROSS REFERENCE TO RELATED APPLICATIONS

This application is a divisional application of U.S. patent application Ser. No. 13/654,388, filed on Oct. 17, 2012, which claims priority to U.S. Provisional Patent Application Ser. No. 61/547,908, filed on Oct. 17, 2011, the contents of each prior application are incorporated by reference in their entirety herein.

FIELD

The subject matter described herein generally relates to managing infrastructure data from a variety of sources. Specifically, the subject matter described herein relates to managing pipe segment data and related infrastructure data.

BACKGROUND

A large amount of infrastructure data (e.g. relating to a network of pipes) exists. For example, this infrastructure data may include information regarding various conditions of the pipes, locations of the pipes within a network, methods of repairing, cleaning, or replacing the pipes, costs associated therewith, maintenance schedules, and the like.

There are many contexts in which a condition of a pipe is of importance. For example, every year, wastewater managers must make decisions about which portions of their collection system should be maintained, rehabilitated or replaced. The Environmental Protection Agency (EPA) and American Society of Civil Engineers (ASCE) both project hundreds of billions of dollars of investment shortfalls facing aging wastewater infrastructure. Thus, it is important that wastewater managers are able to spend their limited funds most wisely to reduce risks and maintain service levels at a low cost.

In the example context of managing a municipal wastewater collection system, a wastewater manager faced with a limited budget makes prioritization and investment decisions based on the best information available at the time. Unfortunately, although a large amount of information may be available, this information is often difficult to access and analyze and thus is often unusable. This is due to lack of adequate technology for providing accurate representations of the condition of the pipe sections making up the collection system and the absence of systems and methods for organizing and analyzing the infrastructure data.

BRIEF SUMMARY

In summary, one aspect provides a method, comprising: storing an infrastructure project summary report with one or more other infrastructure project reports pooled in a database of project summary reports; the infrastructure project report being prepared via accessing fluid conveyance infrastructure summary data describing a condition of a fluid conveyance infrastructure segment; and using a processor of an electronic device to match the infrastructure project summary report with one or more other infrastructure project reports pooled in the database of project summary reports.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
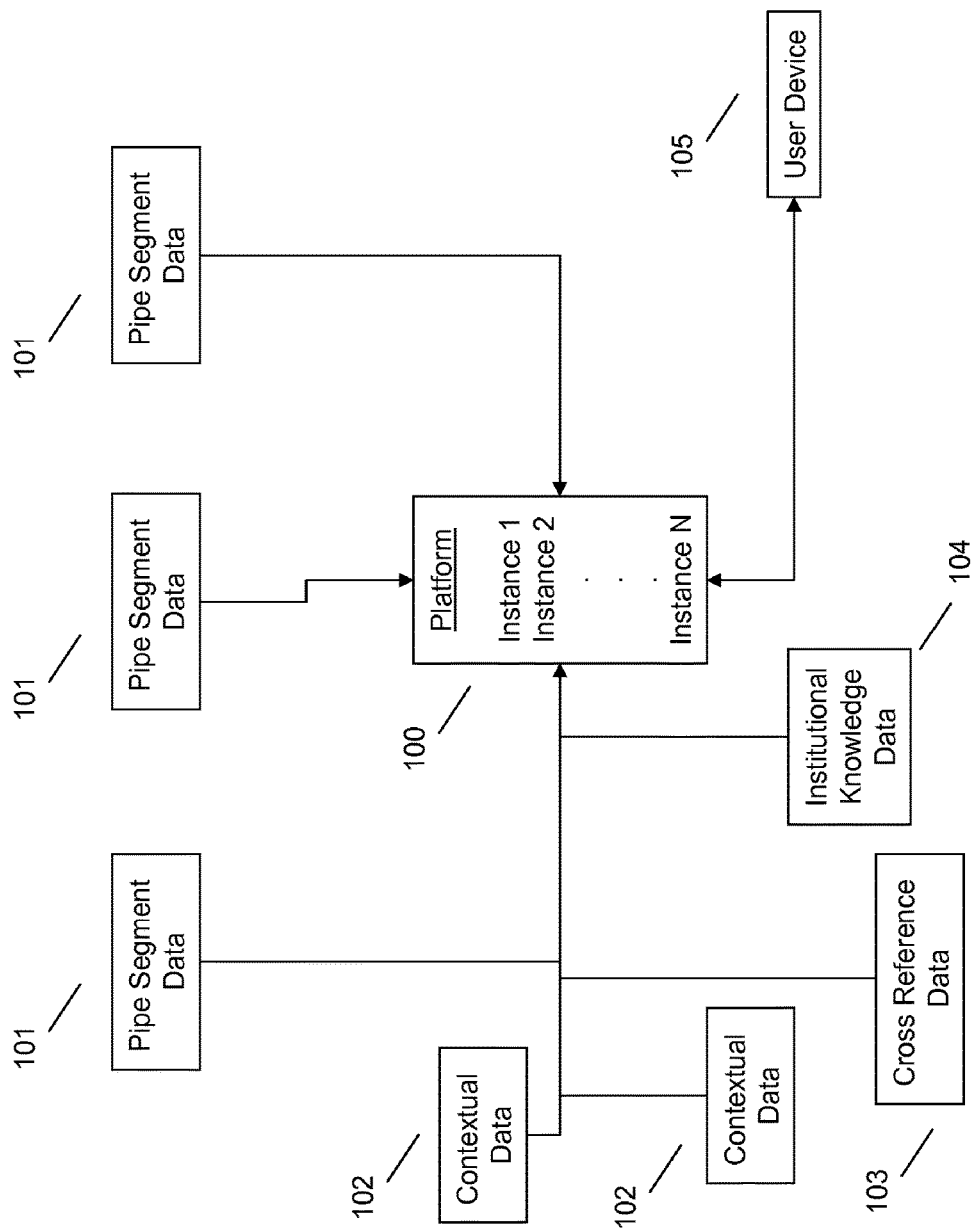
FIG. 1 illustrates an example platform system for analyzing infrastructure data.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the claims, but is merely representative of those embodiments.

Reference throughout this specification to "embodiment(s)" (or the like) means that a particular feature, structure, or characteristic described in connection with the embodiment is included in at least one embodiment. Thus, appearances of the phrases "according to embodiments" or "an embodiment" (or the like) in various places throughout this specification are not necessarily all referring to the same embodiment.

Furthermore, the described features, structures, or characteristics may be combined in any suitable manner in one or more embodiments. In the following description, numerous specific details are provided to give a thorough understanding of example embodiments. One skilled in the relevant art will recognize, however, that aspects can be practiced without one or more of the specific details, or with other methods, components, materials, et cetera. In other instances, well-known structures, materials, or operations are not shown or described in detail to avoid obfuscation.

Especially in critical large-diameter trunks and interceptors, visual-only inspection of pipes, such as using CCTV, is often unreliable and leaves decision-makers with the tough task of evaluating which pipes might appear to be deteriorating. With costly rehab decisions at stake, wastewater managers need facts on infrastructure data, e.g. corrosion severity, not just visual evidence of potential problems.

Underground infrastructure, as further described herein, involves the need to access and collect data in a variety of structures. In this regard, as used herein the terms "fluid conveyance infrastructure" or simply "infrastructure", have the meaning of water and/or sewer physical infrastructure, including pipes, manholes, laterals, access shafts, junction chambers, valve chambers, and treatment structures.

Co-pending and commonly assigned U.S. patent application Ser No. 13/654,376, entitled "GRAPHICALLY REPRESENTING A CONDITION OF INFRASTRUCTURE", filed Oct. 17, 2012, incorporated by reference herein, describes systems and methods for collection of infrastructure data, processing the infrastructure data and related data, and representing a condition of infrastructure. Infrastructure data may be collected for example using a pipe inspection robot utilizing an architecture similar to that disclosed in U.S. patent application Ser. No. 12/611,641, the contents of which are incorporated by reference herein, or another data acquisition platform, such as the HD Profiler System available from RedZone Robotics of Pittsburgh, Pa. Co-pending and commonly assigned U.S. patent application Ser. No. 13/654,380, entitled "ANALYZING INFRASTRUCTURE DATA", filed on Oct. 17, 2012, describes systems and methods for analyzing infrastructure data, and is incorporated by reference herein. In the presence of precise data describing infrastructure, e.g. the condition of a pipe, many opportunities exist for leveraging such data in managing an infrastructure, such as a wastewater management system.

Embodiments provide systems and methods that allow users to manage infrastructure assets based on objective, reliable measurements (e.g. of the condition of pipe(s)) that are presented in useful, intuitive and easily understood formats. In terms of data collection, embodiments may utilize infrastructure data collected using multi-sensor collection techniques, for example as described in co-pending and commonly assigned U.S. patent application Ser. No. 13/654,376, entitled "GRAPHICALLY REPRESENTING A CONDITION OF INFRASTRUCTURE", filed Oct. 17, 2012. Embodiments may also utilize other data sources, such as contextual data, either separately or in some combination with such sensed data, for example pipe segment location data, service call history data for a pipe segment or type, geographic data (e.g. proximity of pipe segments to water bodies), data indicating inclination/slope of a pipe segment, pipe cleaning data, pipe repair and replacement data, contractor related data, cost data, and the like, as further described herein.

Accordingly, embodiments provide systems and methods for managing infrastructure data that may be leveraged in making decisions, for example decisions regarding preparing of infrastructure project summaries and bid packages, preparing and evaluating of bids, selecting contractors/subcontractors to perform maintenance and rehabilitation work ("infrastructure projects") on infrastructure assets, assessing appropriate methodologies and technologies for the infrastructure projects, and assessing the quality of work following completion of an infrastructure project. Infrastructure assessment results in a large volume and variety of data sets. Embodiments enable a user to understand and make fact-based decisions that are driven by this abundant and rich data. Thus, embodiments provide an option to optimally deploy limited resources in operating, monitoring, managing, maintaining and rehabilitating the infrastructure.

A challenge faced by infrastructure managers is managing the bidding of infrastructure projects to be performed. The infrastructure projects may be performed in house or by third parties, or a suitable combination of the foregoing. There are several risks associated with such work that infrastructure managers should take into consideration.

Certain risks arise from not fully understanding the scope of the infrastructure project. For example, a risk of cost over-run is created if a supplier is underbidding the infrastructure project and fails to understand the actual extent of the work to be performed. A risk of cost over run may similarly be created if a supplier under bids an infrastructure project to win the bid, and subsequently attempts to make up the discrepancy with change orders that increase the scope and cost of the work.

Similarly, suppliers may over bid an infrastructure project to cover for execution risks in situations where there is uncertainty in the scope of the work and change orders are not permitted. If a supplier does not appreciate the scope of the work, the supplier may be unable to finish the infrastructure project and the infrastructure project may have to be re-bid.

Additionally, if a supplier's skills, equipment, techniques or experience are not adequately matched to the actual scope of the work, additional costs may be incurred if an infrastructure project cannot be completed or is completed poorly as a result. In contrast, certain suppliers may appear unqualified based on an inaccurate infrastructure project summary, yet actually be qualified to perform the work that is actually involved in completing the project. A similar result may occur if a supplier is disqualified from an entire project simply because the supplier is not qualified to complete a minor portion of the infrastructure project. This results in inappropriately disqualifying certain suppliers. In certain circumstances, an inaccurate project summary may not be adequately split into component parts and may result in eliminating certain suppliers form working on sub-portions of the project for which they are qualified. If an infrastructure project summary is inaccurate, it may also lead to no bids being submitted, as the scope and content of the infrastructure project may be unclear or appear undesirable to suppliers that are actually qualified and available to perform the work.

Accordingly, embodiments provide systems and methods for accurately understanding the scope of the work involved in an infrastructure project to ensure that the project summaries are appropriately tailored to the actual work that needs to be completed. With an accurate infrastructure project summary, updated for example using precise pipe segment data obtained for a network using pipe inspection robots, infrastructure managers are in a position to accurately determine if the infrastructure project should be completed in-house using resources already available, or whether some or all of the infrastructure project should be put out to bid for completion by third parties. Moreover, accurate infrastructure project summaries will allow suppliers to submit appropriate bids, with services, equipment, cost and timing information more realistically tailored to the actual scope of the work.

Embodiments provide a system that utilizes analysis tools to address these problems and assist infrastructure managers in optimizing their spending and minimizing their execution risks in completing infrastructure projects. Embodiments leverage rich data sets acquired using advanced sensing to provide bidders with better information regarding an infrastructure project, thus allowing the bidders to better understand the scope of the infrastructure project under consideration. As a result, embodiments facilitate bids of increased accuracy and quality.

Embodiments provide a platform in which project summaries and bids may be presented on-line in a web-based collaborative tool or a desktop collaborative tool that synchronizes periodically through the web, that directly transfers bid specific data/parameters and bid specific reports for a wide range of suppliers to bid on.

Measurement data and results gleaned from this data may be used to automatically or semi-automatically develop a detailed bid specification/project summary to exacting quality to reduce bid risk premiums and improve bid results. Likewise, embodiments may be used to evaluate completed jobs using updated pipe segment data, obtained for example by inspecting a rehabilitated pipe after completion of a project.

The description now turns to the figures. The illustrated example embodiments will be best understood by reference to the figures. The following description is intended only by way of example and simply illustrates certain selected example embodiments representative of the invention, as claimed. It should be noted that although wastewater pipes are specifically mentioned as examples herein, the various embodiments may be employed in connection with other pipe segment types and other comparable infrastructure assets generally.

Referring to FIG. 1, an embodiment provides a platform 100 that receives infrastructure data from a variety of sources. For example, the platform 100 receives pipe segment data 101, i.e. data collected with pipe inspection robot(s) at a given time and synchronized with a particular location within a pipe segment (either at the time of collection in a post processing procedure). The platform 100 may also receive contextual data 100 from a variety of sources, such as remotely connected devices storing relevant infrastructure information. For example, contextual data 100 may include pipe segment location data, service call history data for a pipe segment or type, geographic data indicating proximity of pipe segments to water bodies, data regarding the inclination of a pipe segment, data regarding previous maintenance of pipe segments and contractors, techniques and costs associated therewith, etc. The platform may also receive cross reference data 103, for example reference infrastructure information from other cities, municipalities, etc., as well as best practices data, contractor related data, cost data, and the like. The platform may also receive institutional knowledge data 104, for example text or video notes of an employee familiar with a particular infrastructure asset or feature.

Figure 2:
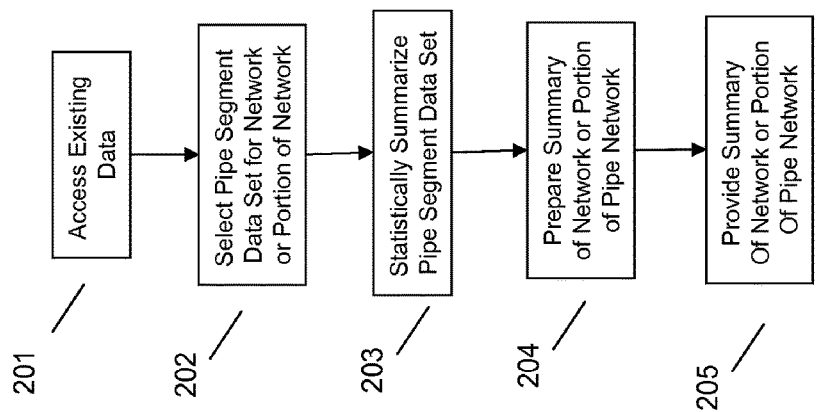
FIG. 2 illustrates an example method of summarizing pipe network data.

Referring to FIG. 2, because inadequate infrastructure project summaries may cause risks associated with inadequately determining the scope of the work involved, an embodiment provides a mechanism to obtain a summary of pipe segments and networks of pipe segments (or portions thereof), thus facilitating a better understanding of the condition of the assets. With such information, asset managers are in a better position to prepare project summaries, bid out projects, and select appropriate suppliers.

An embodiment may access detailed pipe segment data, as well as other relevant infrastructure data at 201, for example as stored in a data base accessible to platform 100. Platform 100 may select from the existing infrastructure data pipe segment data for pipe segments of interest for a particular project at 202. The selection may be based on direct user selection of a network or portion thereof, direct user selection of a particular pipe segment, an automated selection based on a given parameter (e.g. pipes having suffered a certain threshold level of corrosion or sediment buildup, or the like), or a suitable combination of the foregoing.

Responsive to the selection of a network of pipes or a portion thereof, an embodiment may provide a statistical summary 203. For example, if a particular segment of pipe is selected by a user, an embodiment may provide a summary of the condition of that pipe based on the underlying pipe segment data. An example statistical summary may include an average sediment build up statistic for the segment of pipe, an average corrosion level of the segment of pipe or the like. Similar statistical summaries may be prepared for a plurality of pipe segments, portions of networks, or an entire network. Alternatively, the statistical summary may be provided for a network or portion thereof selected automatically in response to a user input parameter, for example a statistical summary of all pipes in a network over a certain age threshold in terms of average corrosion, sediment or the like. Thus, an embodiment may assist an asset manager in understanding the overall condition of the network of a portion thereof in terms of identifying and evaluating appropriate portions for asset management.

Once a statistical summary has been calculated at 203, it may be prepared by an embodiment at 204, for example formatted into a report or graphic, and then provided to a user at 205. Thus, an embodiment provides accurate summaries of the condition of pipe segments, portions of a network of pipes, or an entire pipe network for the user. Such fact-based summaries of pipe conditions helps address risks associated with an asset manager not fully appreciating the scope of work involved in an infrastructure project, as the asset manager will be apprized of the actual condition of the pipes prior to preparing an infrastructure project summary.

Figure 2A:
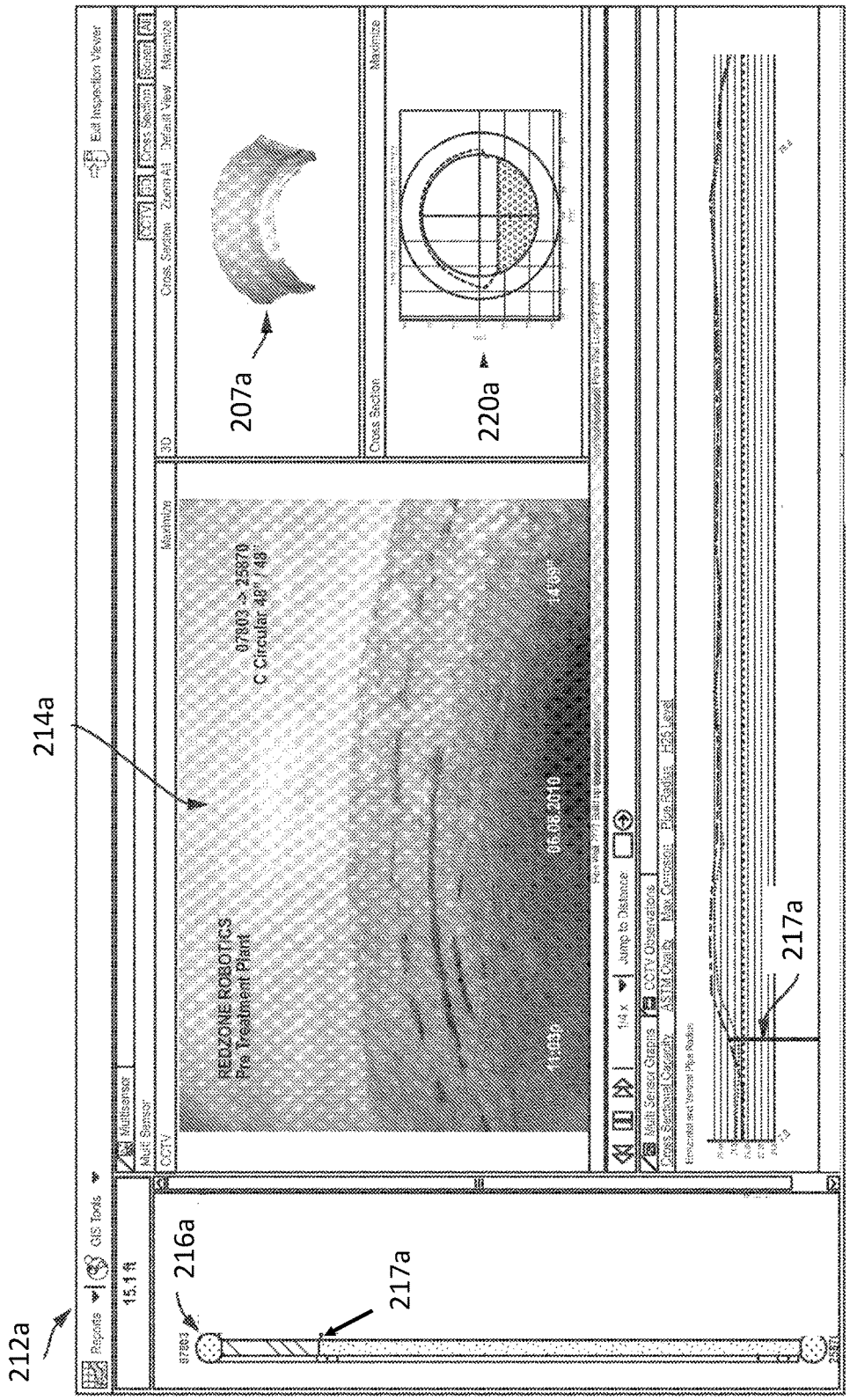
FIG. 2A illustrates an example view according to an embodiment.

An embodiment may combine the various data in various user displays. For example, illustrated in FIG. 2A is a view 212a wherein a CCTV image 214a for a particular segment of pipe is provided. The segment of pipe for which data is loaded in this particular view 212a is provided in a left panel, i.e. between two manholes 216a. The exact portion of the pipe segment being viewed currently is illustrated by an indicator 217a, which provides easy reference to the user for understanding exactly which pipe segment portion the CCTV image was obtained from, due to synchronizing the pipe inspection robot's data collection activities with a physical location with the pipe segment. The indicator 217a may be synchronized in several panels, for example in the lower panel (illustrating vertical and horizontal pipe diameters in X-Y graph form in this example). Moreover, the cross-sectional graphic 220a and 3D graphic 207a are likewise synchronized with the portion of the pipe segment indicated by the indicator 217a.

The sensed data may be processed in a variety of ways to provide useful presentation of the data representing the condition of a pipe. An example process begins with cross sectional data gathered during inspections of pipelines using a pipe inspection robot (more than one may be deployed in a given pipe or network of pipes). According to various embodiments, a cross section may be collected approximately every 10 millimeters, although shorter intervals can be used. The cross-section is then digitized by 180 radial measurements to give a circumferential representation of the pipeline, more or less radial measurements could be used by various embodiments. The cross-sectional data may be visually overlaid with the (known) original pipeline shape (or previously measured pipe shape, a comparison pipe shape obtained from cross-reference data, or the like) and the variance data from this reference is ascertained.

Risks of cost over runs due to supplier underbidding the project for failing to understand the extent of work to be performed is a common problem faced by infrastructure managers and cities. Repair and rehabilitation contracts may come in much higher than initially budgeted if the project summary is inaccurate. For example a city might put out a bid for large diameter pipe cleaning. Without knowledge of how much sediment is actually in the pipe, several bids maybe received based on assumed or typical sediment and debris levels. If such bids are accepted by the city and proceed to execution, after completion of a portion of the work, the contractor might observe that the debris levels in the pipe are much higher than anticipated. As a result the contractor may submit a change order for approval by the city indicating that the work cannot be completed per the original bid amount and additional funds would be necessary to complete the project given the actual pipe conditions. This may severely setback the infrastructure manager and city in terms of funding for the project and timeliness of completion.

Accordingly, an embodiment provides a method to avoid this situation by leveraging existing pipe condition assessment data to provide quantitative summaries and reports as part of the bid package to contractors. For instance, if a sonar or sonar and laser pipe condition assessment data was completed by the manager recently, and all the data from this information was available in the database, a very specific summary and report of the pipe conditions may be included in the bid package. Such an updated bid package may include an estimation of total sediment volume (e.g. in cubic yards or truck loads) along with a profile of distribution of the debris in the system (e.g. areas of high sediment and areas of low sediment). With this objective data, the supplier would be able to perform the cleaning work within the allotted time and contract amounts. This greatly reduces the probability of cost overruns and provides better planning and control of maintenance and rehabilitation projects by the city. In this regard, providing an accurate project summary as part of a bid package is useful in ensuring expectations are appropriately set prior to putting a job out to bid.

Figure 3:
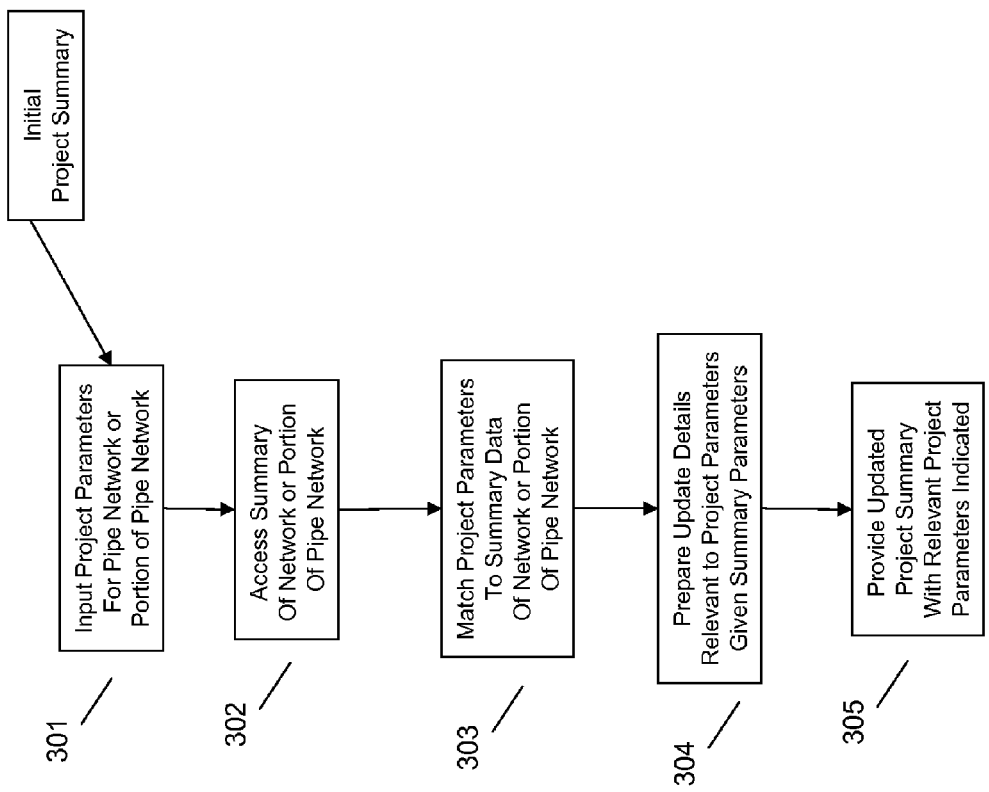
FIG. 3 illustrates an example method of analyzing an infrastructure project summary.

Referring to FIG. 3, an embodiment also may assist a manager in preparing a project summary or determining if a project summary is accurate and reliable prior to its inclusion with a bid package. According to an embodiment, a manager (or other user) may not have a project summary in mind per se, but may know that something is to be done (e.g. cleaning, repair, or other maintenance) to a particular pipe, portion of a infrastructure network, or entire network. Accordingly, and embodiment may provide a mechanism for gathering accurate summary data regarding the condition of the pipe, portion of the infrastructure network, or entire network such that the user may accurately summarize the work to be done (e.g. for inclusion within a bid package).

On the other hand, a user may have an idea of the type of project (e.g. cleaning), but need more information about the extend or type of project (e.g. how much cleaning, what type of sediment, what type of pipe material, pipe inclination, location, etc.). Given an initial project summary (including various parameters, such as particular pipe segment(s) to be cleaned), an embodiment may input the project parameters into an analysis tool at 301. Because accurate, fact-based summaries of pipe conditions are available to the system, which may include previously collected infrastructure data (e.g. via sensing data with a data acquisition platform) and/or cross-reference data (e.g. from a similar pipe in another municipality's network), and/or other data, the system may access such summaries at 302 and compare the input project parameters/summary to existing infrastructure data at 303. As described herein, the initial project summary parameters may be as simple as a selection of a particular pipe segment, portion of an infrastructure network, or the entire network. Thus, the system is charged with providing a summary relating to this input parameter. Thus, more or fewer parameters may be included in an "initial" project summary.

Based on the comparison/matching at 303, an embodiment may prepare (or update) one or more of the input project parameters at 304. For example, the comparison/matching may be based on location data, GIS data, pipe segment/sensed data, human input data, institutional knowledge data, contextual data, and/or cross reference data. For example, an embodiment may determine that although the initial project summary did not indicate a level of sediment in the pipe, the actual pipe condition (based on the summary derived from pipe segment data) indicates that sedimentation is moderate to high level, and thus more than "average" cleaning will be required. An embodiment may provide an update to these types of project parameters at 304 and provide an updated project summary at 305 to be included in the bid package.

Such an updated project summary may negate risks such as a risk of cost over runs due to supplier underbidding the project to win bid and subsequently trying to make up ground with change orders that increase scope and cost. In the cleaning example, without quantitative, objective data as part of the bid package a supplier could leverage the inherent unknowns in pipe condition and the ability to change order to intentionally underbid a project heavily up front. Such a scenario may frustrate efficient cleaning and keeping cost low. Utilizing an embodiment, this situation could be avoided by providing quantitative assessments of the amount of cleaning work required based on measured sediment levels, disallowing change orders once work has commenced.

Excessive cost mark up by a supplier to cover for execution risk in situations where change orders are not permitted may also be mitigated by embodiments. In the cleaning example, without quantitative, objective data as part of the bid package, restricting change orders could have a detrimental result. Due to the inability to change order, all the bidders would tend to assume the worst case pipe condition to limit their exposure. This could result in highly inflated bids, and prevent the city from even embarking on the project. Thus, an embodiment may provide increased confidence in making a determination to allow or disallow change orders give the data relating to existing pipe conditions. For example, this situation may be avoided by using quantitative assessments of the amount of maintenance or rehabilitation work required, ensuring that all bidders are pricing to those accurate levels and are not being excessively conservative and inflating bids to cover for the risk.

Likewise, an embodiment also mitigates risks concerning the inability of a supplier to complete job due to lack of comprehension of scope, which may result in re-bidding needs and cost escalation. In the cleaning example, based on the amount of sediment in the pipes, different cleaning technologies or systems may be required. For instance the type of sediment, the localization of sediment, etc., may impact if the pipe could be cleaned by flushing, jetting or would need a more positive material removal process like a bucket machine. An embodiment provides a quantitative, objective data based assessment regarding the type and quantity of sediment, the distribution of sediment, the volume of sediment, etc., based on the available pipe segment data. An embodiment thus allows such assessments to be included as part of the bid package. Because different bidders might propose different cleaning technologies, and the low bidder selected on the project might commence the work and find out that their cleaning process is ineffective for the specific condition without such information being included, this could result in the project requiring a re-bid.

An embodiment thus permits this situation to be avoided by providing quantitative data as part of bid package. This shifts the burden from the asset manager to the bidders and puts the onus on the providers to bid with the most suitable technologies for the actual work involved.

Figure 4:
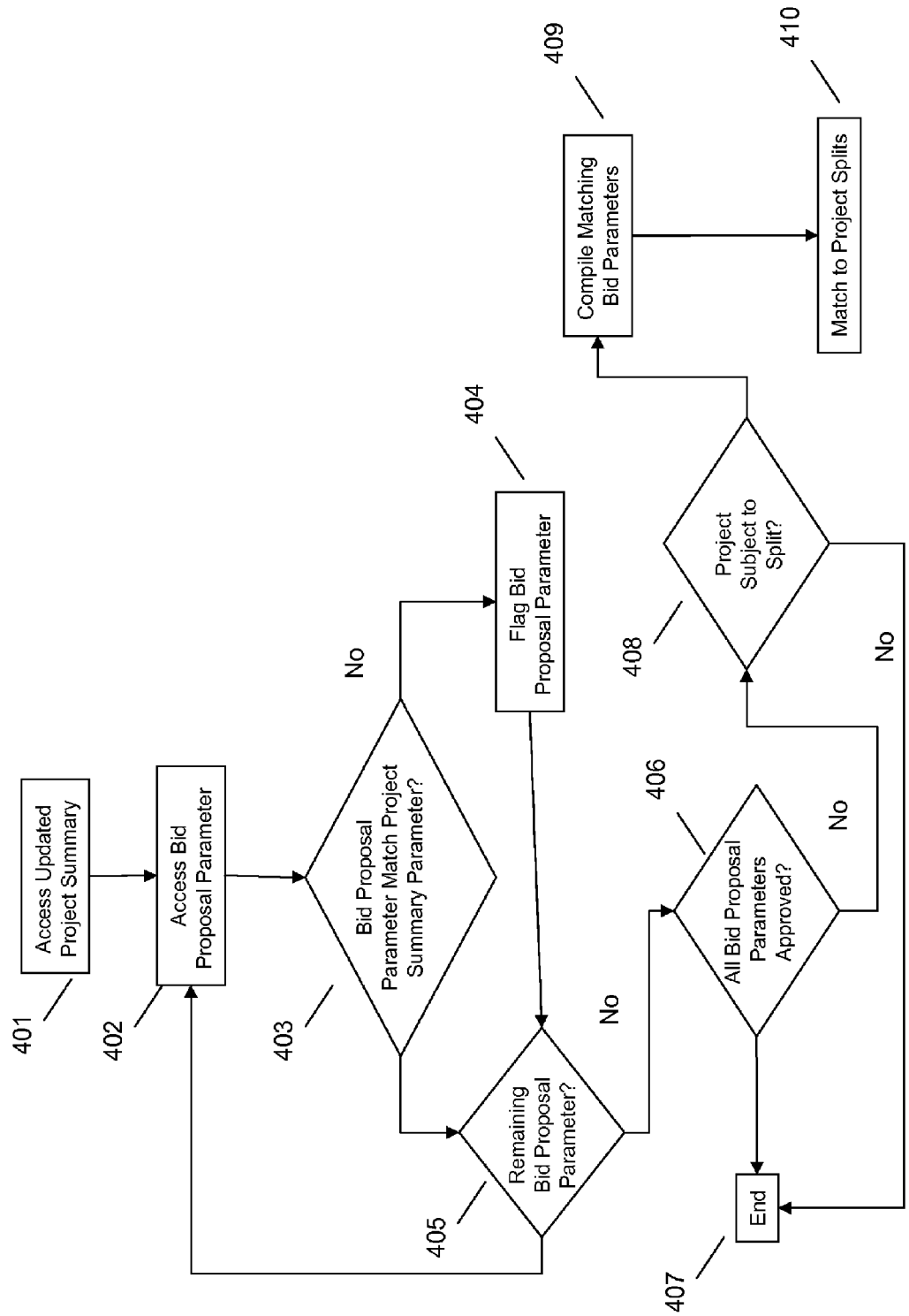
FIG. 4 illustrates an example method of analyzing a bid on an infrastructure project.

An embodiment provides for automated evaluation of bids based on such parameters. Referring to FIG. 4 for example, an embodiment may access a project summary and a bid at 401 and 402, respectively, and extract parameters from each. An example parameter may be a particular technology for cleaning a sediment filled pipe, such as jetting. At 403, an embodiment may determine if the bid proposal parameter matches the corresponding project summary parameter. If not, then the bid parameter may be flagged at 404. In either event, the process may iterate through remaining parameters for comparison if it is determined that there are parameters remaining at 405. If no parameters are remaining for comparison, an embodiment may determine if all or less than all parameters of the bid appropriately match those called for in the summary at 406. If so, the bid may be considered a strong candidate for acceptance and the process may end 407.

However, if all parameters did not match, an embodiment may consider if the project is subject to splitting at 408. For example, the project summary may indicate that for particular pipe segments jetting is not required given the sediment condition of those pipes, and that an alternative may be acceptable. Thus, even though a flagged parameter from the bid was discovered, an embodiment may consider if the flagged parameter may be reconciled, e.g. through splitting the project. If so, an embodiment may compile the flagged parameters of the bid that match alternatives if splitting the project were employed 409, and map the pipe segments or project portions having parameters that the bid parameters may be acceptable for at 410.

Such an approach may mitigate the risk of elimination of suppliers that could be good candidates to execute a specific job or portion thereof, but are disqualified due to inability to meet a small portion of the project specification/summary. For example, a common problem with bids issued by cities are that a large amount of work is bundled into a single project which necessitates every bidder to have the capabilities to handle all of the specified work as the prime, and subcontract any work that the prime cannot fulfill. In the cleaning example, the summary could include cleaning of pipes from sizes 6" through 120". Generally different technologies are used for different range of pipe sizes and it is rare for the same technology or cleaning process to be applicable to this entire scope. So if a bidder specializes in only cleaning large diameter pipe from 24" and above, they would not be able to bid (or bid accurately) on this project without partnering with another contractor that can perform the remaining work. This kind of subcontracting results in the typical problem of margin stacking where the prime contractor marks up pricing from the subcontractor without adding any value and the city incurs higher costs for the project.

Accordingly, an embodiment provides a mechanism to allow the bidders to submit bids that will be considered on parts of the infrastructure project that they are equipped to handle. An embodiment thus allows the system to split the bids according to project summary parameters into a more focused area that allows specialty contractors to bid on the project without incurring margin stack.

Risk of supplier capabilities and experience being inadequate resulting in poor execution may also be mitigated by an embodiment. A common problem with contract awards by cities to contractors is to have an independent and common measure of the quality and cost effectiveness of work by different contractors. Cities typically specify stringent reference and past work history requirements as part of the bid submission, but there is no common framework for the city to evaluate the past work history quality and cost effectiveness of work by different contractors.

In an embodiment, activities of providers may be tracked across different cities such that a comprehensive work history evaluation can be built for each contractor and made available through the platform 100. The measures or key performance indicators (KPI) may be tracked as percentages of cost overruns for past projects, percent schedule slip for past projects, number and type of failure-to-meet-quality issues from past projects, a numerical rating (e.g. 1-5 or similar rating) of overall satisfaction from the city for a supplier's work, number of years and volume of experience with specific capabilities or technologies, or the like. These scores may be compared across bidders individually and an overall suitability rating may be generated for each bid based on their scores tracked in the data base.

Embodiments also mitigate the risk of wrong choice of rehabilitation method specified due to lack of sharing of best practices and failure/success stories across asset owners. Rehabilitation, inspection and other technologies are constantly evolving and often times bid specifications lag behind the latest technological advances, or do not leverage past successes and failures for different rehab methodologies. By virtue of platform 100, asset managers will have access to relevant infrastructure data in this regard, for example contextual data 102, cross reference data 103, and/or institutional knowledge data 104 that may be shared between users of the platform 100.

Embodiments also facilitate appropriate selection of methodologies based on available pipe segment data, such as pipe slope and pipe bend/curve data available to the platform 100. Different rehabilitation, maintenance and repair approaches have different key indicators for project success. For instance a chemical root treatment project is dependent on slope of pipes, since if there is inadequate slope in the pipe, the chemical cannot adequately be distributed in the system. Additionally the slope determines the interval or distance between locations where the chemical will be introduced into the system. Similarly, for a slip lining refurbishment, data on pipe bend angles and bend extents can be provided. An embodiment may thus include the data for both of these two disparate reports (slope vs. bend radius), as derived from the same inherent multi-sensor-inspection based data sets. Based on the type of rehabilitation project being set up, e.g. slip lining or chemical root treatment, an embodiment may automatically recognize the most relevant parameters or metrics for the infrastructure project (in this example, bend radius or pipe slope). As such, these may be taken into consideration and included in the summary of pipe condition, and be used to update a project summary accordingly for inclusion in a bid package.

Figure 5:
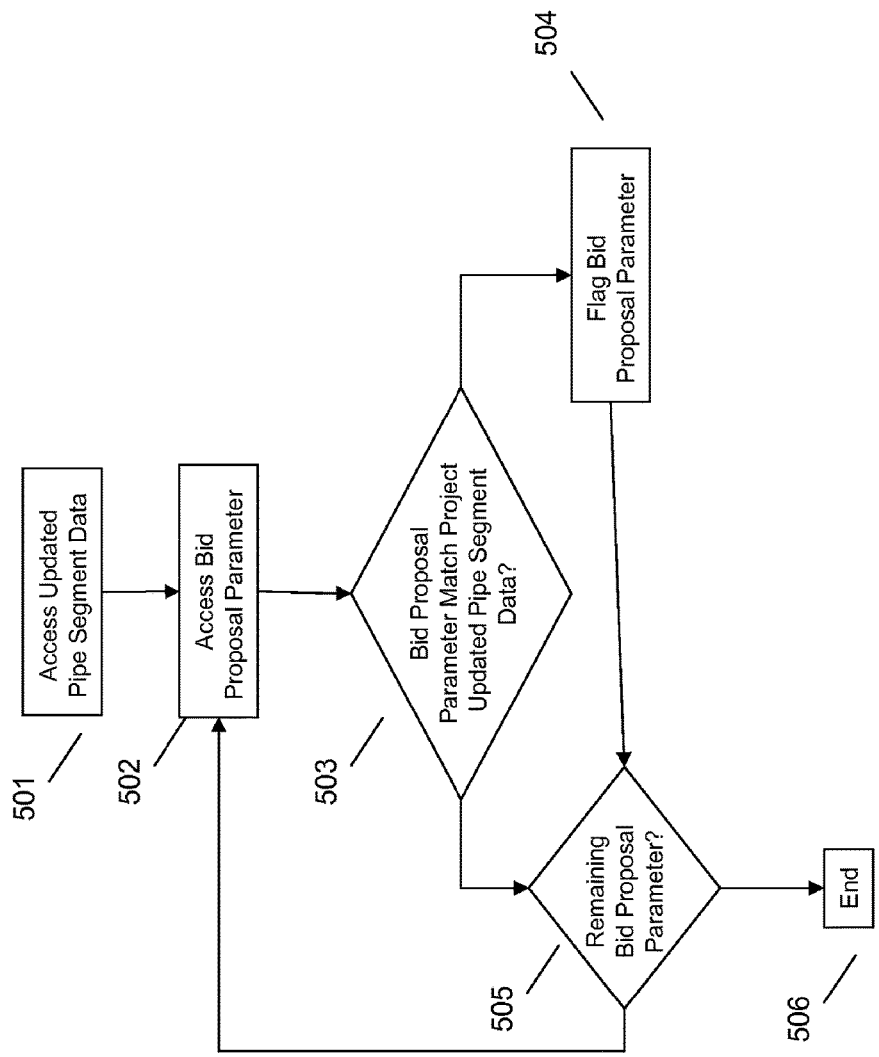
FIG. 5 illustrates an example method of evaluating a completed infrastructure job against original expectations.

Referring generally to FIG. 5, a common challenge for infrastructure managers is to determine the quality of rehabilitation work after the project has been completed. This could be either for quality assurance, for acceptance or rejection of particular rehab work, or it could be for future reference use by the infrastructure manager to see how effective the technology or supplier was, etc.

An example of quality assurance use is that of laser profiling of newly installed plastic pipe. Laser profiling is used to ensure that the ovality of the pipe is less than a certain amount to confirm that the pipe was adequately back filled during installation. In this case, given a project summary calling for installation of plastic pipe, after the supplier has installed the new pipe, a laser profiler based pipe assessment may be completed and stored.

An embodiment may access this updated pipe summary data at 501 and the bid proposal (or other relevant data indicating the expected result) at 502 and determine if these match at a given threshold at 503 as a criteria for acceptance of the pipe work. If the results are out of threshold acceptability parameter(s), the parameter may be flagged by an embodiment at 504 indicating the problem. The city may then require the supplier to re-install the pipe and perform another verification inspection. An embodiment may likewise step through various parameters at 505 until all have been analyzed and the job assessment process ends at 506.

Another example of quality assurance that may be used is to perform sonar profiling based pipe assessment after a pipe has been cleaned to ensure that the sedimentation that was required to be removed as part of the project was removed. Utilizing an embodiment, the results of all of these post construction verifications can be stored in the database and associated to the technology, the provider, size of pipe segment, type of pipe, etc. These results can then be queried using the platform 100 for future projects to ensure the most appropriate technology and most appropriate providers are engaged for the projects.

A consideration for infrastructure managers is to determine if a specific project should be bid out for fulfillment by third party providers or if it should be completed in-house. These decisions are similar to make-versus-buy decisions faced by most entities. Using an embodiment, such decisions may be handled procedurally by treating the various options, including an in-house option, as one of the bids. Then the in-house option may be evaluated to all other bids and the most cost-effective decision pursued. Consideration of fixed costs versus variable costs for the in-house option may be important for such evaluations and may be accounted for during the evaluation. For example if the city has a cleaning truck, with labor availability, the variable costs for it to pursue a cleaning project internally may be much lower than a third party contract option, and this would be derived from such analysis.

A problem encountered by infrastructure managers in the smaller cities is the inability to solicit bids from and non-local large contractors due to the smaller size of their project scope. For instance, a city may just need 10,000 ft of pipe relined or cleaned. This might be too small a volume and not attract bids from larger regional contractors due to their higher mobilization costs as compared the volume of work.

Figure 6:
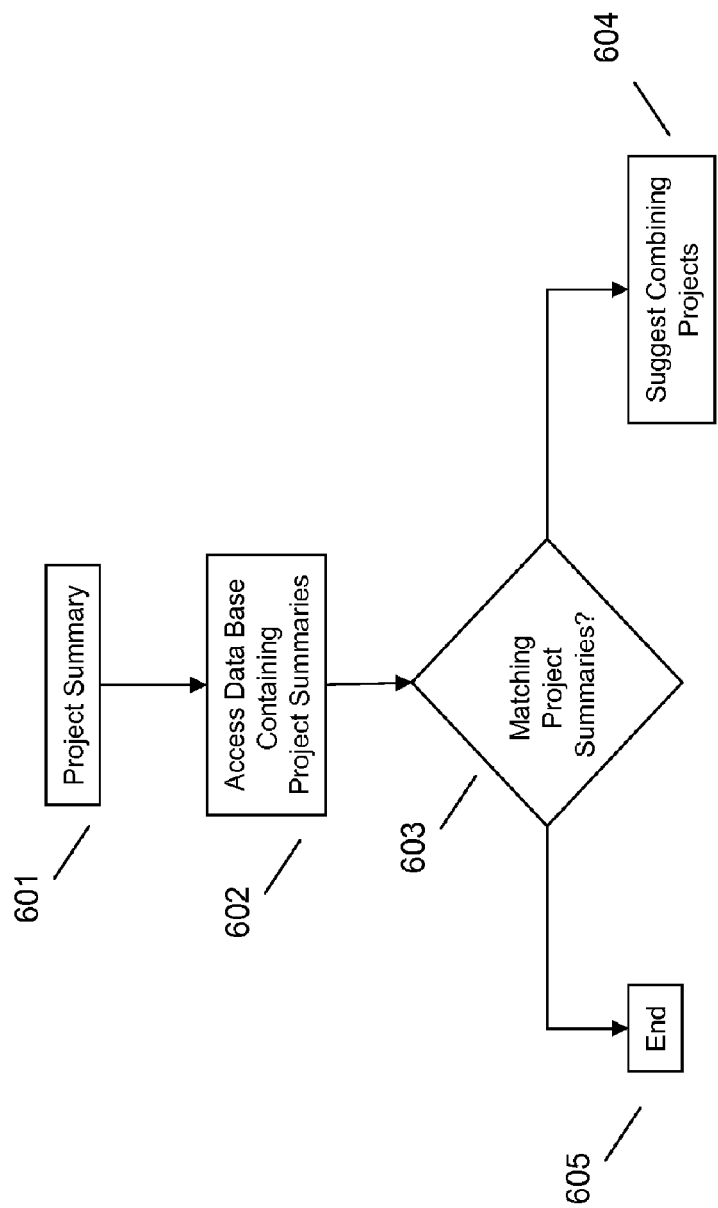
FIG. 6 illustrates an example of method of pooling infrastructure project summaries for combined bidding.

Referring to FIG. 6, an embodiment provides infrastructure managers with an option to pool their projects with other projects from other cities (e.g. geographically proximate, etc.) such that in totality the project scope increases significantly. This is somewhat similar to the inverse of splitting a project. Such collaboration may entice larger regional contractors to bid on the projects. Accordingly, given a project summary at 601 (including parameters such as pipe diameter, pipe cleaning technique, sediment amount, etc.), an embodiment may search data base(s) available at 602, e.g. via the platform 100, to determine if there are any similar or matching projects in other municipalities at 603. If so, an embodiment may provide an indication of the matches and suggest a collaboration or combining of projects at 604. Otherwise, the process may end at 605.

Analogously, an embodiment may serve as an intermediary to pool together project scopes from numerous smaller projects and negotiate preferred pricing from larger regional contractors that the smaller cities would not be able to achieve with their smaller volumes.

Another problem encountered by suppliers that perform work for cities is ensuring that they have adequate work to keep their assets utilized. In an embodiment, suppliers may be provided visibility into demand for their services in a much broader area and much more comprehensively than they would otherwise be able to find, by virtue of access to the platform 100 containing various project summaries, which may be searchable across parameters of interest to the suppliers. This also allows the suppliers to propose lower pricing for their services based on their presence in a specific region or based on unused capacity. Such exchange between suppliers and asset owners will foster a much more optimal match of supply and demand for these services Another problem encountered by infrastructure managers is a lack of knowledge on the best available technologies for the particular project scope. According to an embodiment, engineering firms and manufacturers of different equipment can specify for their technologies to be described anytime their technology would be applicable via a matching function between technology and specific project parameters of existing project summaries, as facilitated by the platform 100. For example, when an infrastructure manager specifies a relining project via uploading of project summary to platform 100, a best practices guide on relining developed by an engineering firm could be presented along with applicable technologies from equipment providers by virtue of platform 100 automatically matching it with the project summary and/or user account submitting the relining project summary. An embodiment may also serve as a central repository for all such information that is shared with different parties based on the capabilities required for different projects Additionally, an embodiment may facilitate decisions regarding use of appropriate providers, including another asset owner rather than a private/third party supplier. For example, if City A issues a cleaning contract for bid, a series of third party contractors may bid on this project for a given price, but City B, also having access to the platform 100, may have a cleaning truck and operator not being utilized. An embodiment may automatically recommend or facilitate communication such that City B could offer services or bid on City A's project.

Accordingly, various embodiments facilitate managing infrastructure assets. The embodiments leverage infrastructure data and facilitate fact-based summaries of assets and infrastructure projects related thereto.

Figure 7:
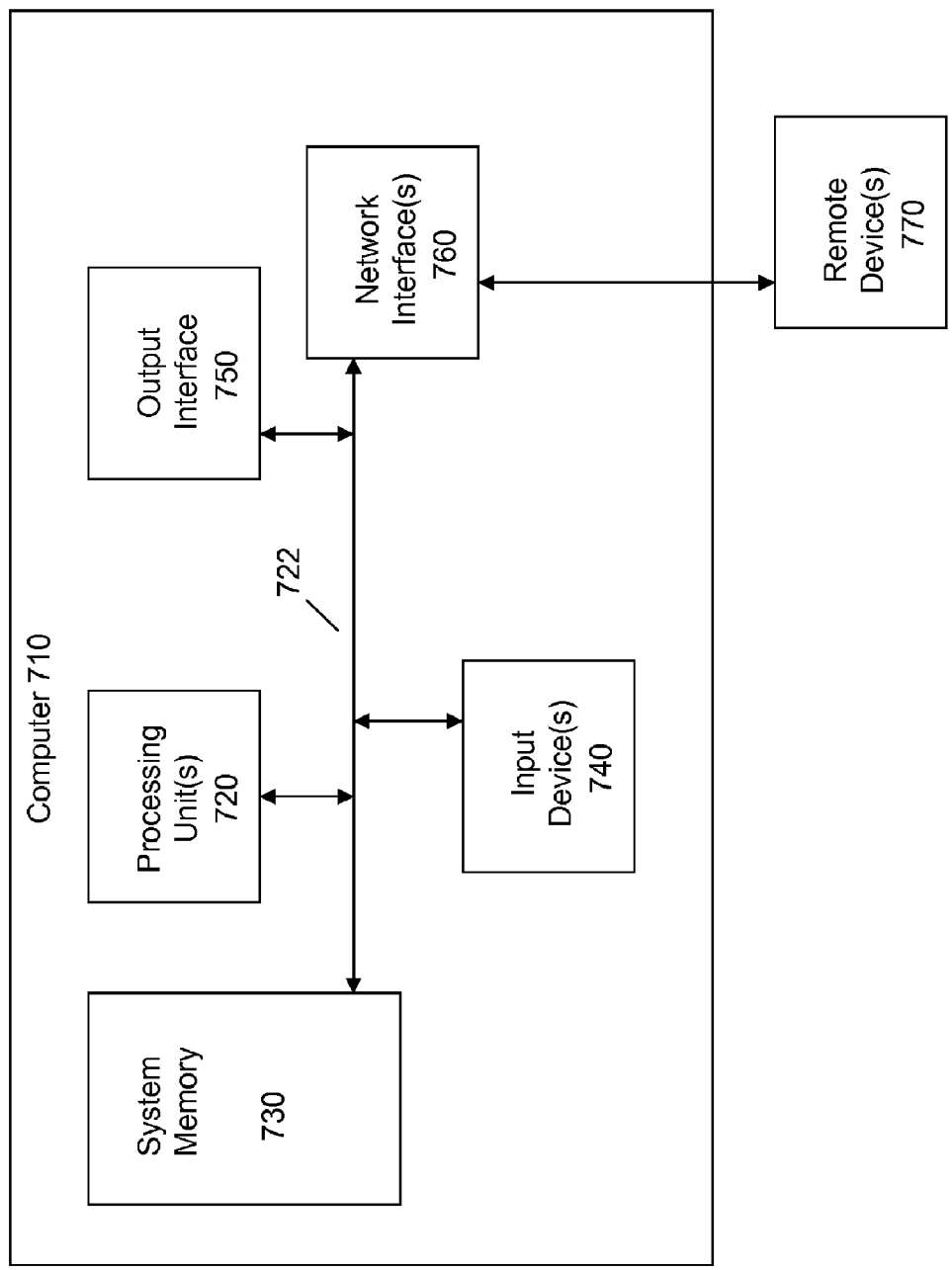
FIG. 7 illustrates an example computing device.

It will be readily understood that certain embodiments can be implemented using any of a wide variety of devices or combinations of devices. Referring to FIG. 7, an example device that may be used in implementing one or more embodiments includes a computing device (computer) 710, for example hosting the platform 100. In this regard, the platform 100 may be provided as a central portal for user access, wherein hosted services (data storage, data analysis, data summary and querying, and the like) are provided. For example, platform may provide a web-based access portal where a user may log in to an account instance and access pipe network and related data to access the functionality of the platform 100 described herein. Alternatively, the platform 100 may be provided as desktop or tablet application, for example that may be downloaded onto a client device such as computer 710.

The computer 710 may execute program instructions configured to store an analyze segment data, and perform other functionality of the embodiments, as described herein.

Components of computer may include, but are not limited to, a processing unit 720, a system memory 730, and a system bus 722 that couples various system components including the system memory 730 to the processing unit 720. The computer 710 may include or have access to a variety of computer readable media, for example for storing infrastructure data indices. The system memory 730 may include computer readable storage media in the form of volatile and/or nonvolatile memory such as read only memory (ROM) and/or random access memory (RAM). By way of example, and not limitation, system memory 730 may also include an operating system, application programs, other program modules, and program data.

A user can interface with (for example, enter commands and information) the computer 710 through input devices. A monitor or other type of device can also be connected to the system bus 722 via an interface, such as an output interface 750. In addition to a monitor, computers may also include other peripheral output devices. The computer 710 may operate in a networked or distributed environment using logical connections to one or more other remote computers or databases. The logical connections may include a network, such local area network (LAN) or a wide area network (WAN), but may also include other networks/buses.

It should be noted as well that certain embodiments may be implemented as a system, method or computer program product. Accordingly, aspects may take the form of an entirely hardware embodiment, an entirely software embodiment (including firmware, resident software, micro-code, et cetera) or an embodiment combining software and hardware aspects that may all generally be referred to herein as a "circuit," "module" or "system." Furthermore, aspects may take the form of a computer program product embodied in one or more computer readable medium(s) having computer readable program code embodied therewith.

Any combination of one or more computer readable storage medium(s) may be utilized. A computer readable storage medium may be, for example, but not limited to, an electronic, magnetic, optical, electromagnetic, infrared, or semiconductor system, apparatus, or device, or any suitable combination of the foregoing. More specific examples of the computer readable storage medium would include the following: a portable computer diskette or memory stick, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible, non-signal storage medium that can contain or store a program for use by or in connection with an instruction execution system, apparatus, or device.

Computer program code may be propagated by data signal for transmission between devices. Such a propagated signal may take any of a variety of forms, including, but not limited to, electro-magnetic, optical, or any suitable combination thereof. Program code embodied on a computer readable storage medium thus may be transmitted using any appropriate medium, including but not limited to wireless, wireline, optical fiber cable, RF, et cetera, or any suitable combination of the foregoing.

Computer program code for carrying out operations for various aspects may be written in any combination of one or more programming languages. The program code may execute entirely on a single computer (device), partly on a single computer, as a stand-alone software package, partly on single computer and partly on a remote computer or entirely on a remote computer or server. In the latter scenario, the remote computer may be connected to another computer through any type of network, including a local area network (LAN) or a wide area network (WAN), or the connection may be made for example through the Internet using an Internet Service Provider.

It will be understood that various functionality described herein may be implemented by computer program instructions. These computer program instructions may be provided to a processor of a device to produce a machine, such that the instructions, which execute via the processor create means for implementing the functions/acts specified.

These computer program instructions may also be stored in a computer readable storage medium that can direct a device to function in a particular manner, such that the instructions stored in the computer readable storage medium produce an article of manufacture including instructions which implement the function/act specified.

The computer program instructions may also be loaded onto a device to cause a series of operational steps to be performed on the device to produce a device implemented process such that the instructions which execute on the device provide processes for implementing the functions/acts specified.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Although illustrated example embodiments have been described herein with reference to the accompanying drawings, it is to be understood that embodiments are not limited to those precise example embodiments, and that various other changes and modifications may be affected therein by one skilled in the art without departing from the scope or spirit of the disclosure.

What is claimed is:

1. A method, comprising:
traversing, using a pipe inspection robot, an interior of a pipe in a municipal water or sewer pipe network, wherein the pipe inspection robot comprises one or more of a camera, a laser sensor, and a sonar sensor;
collecting, using the pipe inspection robot, multi-sensor pipe segment data relating to an interior of the pipe, wherein the multi-sensor pipe segment data comprises two or more of laser pipe condition assessment data, visual images, and sonar pipe condition assessment data;
displaying, on a device screen, the multi-sensor pipe segment data, the displaying comprising providing a view comprising an image of the interior of the pipe, a cross-sectional graphic of the interior of the pipe, and a pipe graphic having an indicator;
the image, the cross-sectional graphic, and the indicator being synchronized with a physical location within the pipe;
generating, using a processor, fluid conveyance infrastructure summary data comprising the multi-sensor pipe segment data formatted into a statistical summary of one or more of sediment level and corrosion level for a least a part of the pipe network;

providing, to a user device, a graphic comprising the statistical summary data of one or more of the sediment level and the corrosion level;

storing an infrastructure project summary report comprising the fluid conveyance infrastructure summary data with other infrastructure project summary reports pooled in a database of project summary reports;

providing, in the view, a link to the infrastructure project summary report;

receiving, at the user device, a selection identifying the project summary report;

querying the database of project summary reports based on the selection;

thereafter receiving, at the user device, at least one of the other infrastructure project summary reports pooled in the database that matches the statistical summary data of the pipe network; and automatically indicating at the user device that the infrastructure project summary report and the at least one of the other infrastructure project summary reports are related based on analysis of statistical summary data for different pipe networks.

2. The method of claim 1, further comprising, responsive to matching the infrastructure project summary report with one or more other infrastructure project summary reports pooled in the database of project summary reports, communicating to one or more users a proposed pooling of infrastructure projects.

3. The method of claim 2, further comprising, receiving an indication from the one or more users that the proposed pooling of infrastructure projects has been accepted.

4. The method of claim 3, further comprising, responsive to receiving the indication from one or more users, preparing a pooled project summary report.

5. The method of claim 4, further comprising, responsive to preparing a pooled project summary report, transmitting the pooled project summary report over a communications network.

6. A method, comprising:
accessing, using a processor of a device, multi-sensor pipe segment data relating to an interior of a pipe in a municipal water or sewer pipe network;
displaying, on a device screen, the multi-sensor pipe segment data;
the displaying comprising providing a view comprising an image of the interior of the pipe, a cross-sectional graphic of the interior of the pipe, and a pipe graphic with an indicator;
wherein the image, the cross-sectional graphic, and the indicator are synchronized with a physical location within the pipe;
generating, using a processor of a device, summary data comprising one or more of sediment data and corrosion data for at least one part of the municipal water or sewer pipe network using the multi-sensor pipe segment data;
providing, in the view, a link to reports comprising the summary data; and
matching, using a processor of a device, summary data of different reports;
wherein one or more reports having similar summary data are retrieved based on the matching.

7. The method of claim 6, wherein the summary data comprises an estimation of total sediment volume in the pipe.

8. The method of claim 7, wherein the estimation of total sediment volume comprises cubic yards of sediment.

9. The method of claim 7, wherein the estimation is provided by a graphic in the view.

10. The method of claim 9, wherein the graphic comprises graphical indication of the number of truck loads associated with removal of the cubic yards of sediment.

11. A method, comprising:
selecting, using a processor of a device, multi-sensor pipe segment data relating to an interior of a pipe in a municipal water or sewer pipe network, the multi-sensor pipe segment data comprising laser condition assessment data and sonar condition assessment data;
the selecting comprising using one or more of a user selection of a pipe network, a user selection of a pipe segment, and an automated selection based on an input parameter selected from the group consisting of a level of corrosion and a level of sediment buildup;
displaying, on a device screen, the multi-sensor pipe segment data;
the displaying comprising providing a view comprising an image of the interior of the pipe, a cross-sectional graphic of the interior of the pipe, and a pipe graphic with an indicator;
wherein the image, the cross-sectional graphic, and the indicator are synchronized with a physical location within the pipe;
generating, using a processor of a device, summary data comprising one or more of sediment data and corrosion data for at least one part of the municipal water or sewer pipe network using the multi-sensor pipe segment data;
providing, in the view, a link to reports comprising the summary data; and
matching, using a processor of a device, summary data of different reports;
wherein one or more reports having similar summary data are retrieved based on the matching.

12. The method of claim 11, wherein the generating comprises:
comparing one or more of laser and sonar radial measurements to predetermined values; and
determining variance data based on differences between the one or more laser and sonar radial measurements and the predetermined values.

13. The method of claim 12, wherein the variance data is converted into the one or more of sediment data and corrosion data.

14. The method of claim 13, comprising visually overlaying expected pipe shape and pipe shape determined from the multi-sensor data.

15. The method of claim 14, wherein the cross-sectional graphic comprises the visually overlaid expected pipe shape and the pipe shape determined from the multi-sensor data.

* * * * *